(12) United States Patent
Hilgenfeld et al.

(10) Patent No.: US 7,956,078 B2
(45) Date of Patent: Jun. 7, 2011

(54) CRYSTAL STRUCTURE OF HUMAN CORONAVIRUS 229E MAIN PROTEINASE AND USES FOR DEVELOPING SARS INHIBITORS

(75) Inventors: Rolf Hilgenfeld, Lüebeck (DE); Kanchan Anand, Lüebeck (DE); John Ziebuhr, Veitschoechheim (DE); Jeroen R. Mesters, Gross-Grönau (DE); Parvesh Wadhwani, Karlsruhe (DE)

(73) Assignee: Universitat zu Luebeck, Luebeck (DE)

( * ) Notice: Subject to any disclaimer, the term of this patent is extended or adjusted under 35 U.S.C. 154(b) by 1346 days.

(21) Appl. No.: 11/273,270

(22) Filed: Nov. 10, 2005

(65) Prior Publication Data

US 2009/0137818 A1 May 28, 2009

Related U.S. Application Data (63) Continuation-in-part of application No. PCT/EP2004/005109, filed on May 13, 2004.

(60) Provisional application No. 60/469,818, filed on May 13, 2003.

(51) Int. Cl.
*A61K 31/422* (2006.01)
*A61K 31/4025* (2006.01)
*C07D 261/08* (2006.01)
*C07D 207/46* (2006.01)

(52) U.S. Cl. ........ 514/378; 514/422; 514/424; 548/248; 548/518; 548/543

(58) Field of Classification Search ............ 514/378, 514/422, 424; 548/248, 518, 543
See application file for complete search history.

(56) References Cited

U.S. PATENT DOCUMENTS 6,906,198 B1 * 6/2005 Dragovich et al. .......... 548/416

OTHER PUBLICATIONS

Matthews et al., Proceedings of the National Academy of Sciences of the United States of America, 1999, 96(20), p. 11000-11007.*
Shie et al., Bioorganic & Medicinal Chemistry, 2005, vol. 13, p. 5240-5252.*
Patani et al., Chem. Rev., 1996, vol. 96, p. 3147-3176.*

* cited by examiner

*Primary Examiner* — Yong Chu
(74) *Attorney, Agent, or Firm* — Diederiks & Whitelaw PLC (57) ABSTRACT

The invention relates to a method of developing a main proteinase SARS inhibitor. Human coronaviruses are major causes of upper respiratory tract illnesses in humans, in particular, the common cold. Recent investigations have shown that a novel coronavirus causes the Severe Acute Respiratory Syndrome (SARS), a disease that is characterized by high fever, malaise, rigor, headache, non-productive cough or dyspnea, which is rapidly spreading. Within the scope of the invention, based on the structural analysis of the binding mode of the SARS $M^{pro}$ enzyme, a group of prototype inhibitors is provided that acts as suitable drugs targeting a majority of viral infections of the respiratory tract, including SARS.

5 Claims, 7 Drawing Sheets
(4 of 7 Drawing Sheet(s) Filed in Color)

CRYSTAL STRUCTURE OF HUMAN CORONAVIRUS 229E MAIN PROTEINASE AND USES FOR DEVELOPING SARS INHIBITORS

PRIOR APPLICATIONS

This application is a continuation-in-part of International Patent Application S.N. PCT/EP2004/005109, filed May 13, 2004, which in turn bases priority on U.S. Provisional Application Ser. No. 60/469,818, filed May 13, 2003.

BACKGROUND OF THE INVENTION

1. Field of the Invention

The invention relates to human coronavirus 229E main proteinase ($M^{pro}$) and uses in the development of inhibitors for Severe Acute Respiratory Syndrome (SARS).

2. Description of the Prior Art

Human coronaviruses (HCoV) are major causes of upper respiratory tract illness in humans, in particular, the common cold. To date, only the 229E strain of HCoV has been characterized in detail because it used to be the only isolate that grows efficiently in cell culture. It has recently been shown that a novel coronavirus causes the Severe Acute Respiratory Syndrome (SARS), a disease that is rapidly spreading from its likely origin in Southern China to several countries in other parts of the world. SARS is characterized by high fever, malaise, rigor, headache, non-productive cough or dyspnea and may progress to generalized, interstitial infiltrates in the lung, requiring incubation and mechanical ventilation. The fatality rate among persons with illness meeting the current definition of SARS is around 15% (calculated on outcome, i.e. deaths/deaths+recovered patients). Epidemiological evidence suggests that the transmission of this newly emerging pathogen occurs mainly by face-to-face contact, although airborne transmission cannot be fully excluded. By May 5, 2003, more than 6400 cases of SARS had been diagnosed world-wide, with the numbers still rapidly increasing. At present, no efficacious therapy is available.

Coronaviruses are positive-stranded RNA viruses featuring the largest viral RNA genomes known to date (27-31 kb). The human coronavirus 229E replicase gene, encompassing more than 20,000 nucleotides, encodes two overlapping polyproteins, pp1a ($\approx$450 kD) and pp1ab ($\approx$750 kD) that mediate all the functions required for viral replication and transcription Expression of the COOH-proximal portion of pp1ab requires ribosomal frame shifting. The functional polypeptides are released from the polyproteins by extensive proteolytic processing. This is primarily achieved by the 33.1-kDa HCoV main proteinase ($M^{pro}$), also called 3C-like proteinase or $3CL^{pro}$, which cleaves the polyprotein at II conserved sites involving mostly Leu-Gln↓(Ser,Ala,Gly) sequences, a process initiated by the enzyme's own autolytic cleavage from pp1a and pp1ab. The functional importance of $M^{pro}$ in the viral life cycle makes this proteinase an attractive target for the development of drugs directed against SARS and other coronavirus infections.

The design of anticoronaviral drugs directed against the viral main proteinases requires the availability of data on the three-dimensional structures of the target enzymes. In 2002, we determined the crystal structure of the $M^{pro}$ of transmissible gastroenteritis virus (TGEV), a coronavirus infecting pigs. The structure revealed that coronavirus $M^{pro}$ consists of three domains, the first two of which together distantly resemble chymotrypsin. However, the catalytic site comprises a Cys-His dyad rather than the Ser-His-Asp triad found in typical chymotrypsin-like serine proteinases.

SUMMARY OF THE INVENTION

We determined the crystal structure, at 2.6 Å resolution, of the free enzyme of human coronavirus (strain 229E) $M^{pro}$, comprising at least a portion of the molecular coordinates deposited at the Protein Data Bank under accession number PDB ID: 1P9S (Coronavirus Main Proteinase (3CLPRO) Structure: Basis for Design of Anti-Sars Drugs). Further, we constructed a three-dimensional model for the $M^{pro}$ of SARS coronavirus (SARS-CoV) based on our crystal structures for HCoV and TGEV $P^{pro}$s, and on the genomic sequence of SARS-CoV.

SARS-CoV $M^{pro}$ shares 40 and 44% amino-acid sequence identity with its TGEV and HCoV counterparts, respectively. We also analyzed the putative cleavage sites of $M^{pro}$ in the viral polyprotein as derived from the genomic sequence based on the molecular coordinates of Transmissible Gastroenteritis Virus (ORF1A) deposited at the Protein Data Bank under accession number PDB ID: 1P9U (Coronavirus Main Proteinase (3CLPRO) Structure: Basis for Design of Anti-Sars Drugs), and found them to be highly similar to those of $M^{pro}$s of HCoV, TGEV and other coronaviruses. Further, we developed a method to produce recombinant SARS-CoV $M^{pro}$ and modifications (mutants), thereof. We show that the recombinant wild-type enzyme exhibits proteolytic activity, while an active-site mutant (C145A) does not. We demonstrate that recombinant SARS-CoV $M^{pro}$ cleaves a pentadecapeptide representing the $NH_2$-terminal autocleavage site of TGEV main proteinase. Comparison of the crystal structures for HCoV and TGEV $M^{pro}$ and the model for SARS-CoV $M^{pro}$ shows that the substrate-binding sites are well conserved among coronavirus main proteinases.

In order to determine the exact binding mode of the substrate and to enable the structure-based design of drugs directed at coronavirus $M^{pro}$, we have synthesized the substrate-analog chloromethyl ketone inhibitor Cbz-Val-Asn-Ser-Thr-Leu-Gln-CMK, the sequence of which was derived from the P4-P1 residues of the $NH_2$-terminal autoprocessing site of HCoV $M^{pro}$. We have determined the 2.37 Å crystal structure of a complex between this inhibitor and porcine transmissible gastroenteritis (corona) virus (TGEV) main proteinase, comprising at least one or more of the following main proteinase sequences:

```
                                                           (SEQ. ID NO: 1)
      1               5                    10                      15
      Ser Gly Leu Arg Lys Met Ala Gln Pro Ser Gly Leu Val Glu Pro Cys
      Ile Val Arg Val Ser Tyr Gly Asn Asn Val Leu Asn Gly Leu Trp Leu
                      20                   25                      30

35                   40                      45
      Gly Asp Glu Val Ile Cys Pro Arg His Val Ile Ala Ser Asp Thr Thr
      Arg Val Ile Asn Tyr Glu Asn Glu Met Ser Ser Val Arg Leu His Asn
                     50                   55                      60
```

-continued

```
             65                      70                      75                      80
Phe Ser Val Ser Lys Asn Asn Val Phe Leu Gly Val Val Ser Ala Arg
Tyr Lys Gly Val Asn Leu Val Leu Lys Val Asn Gln Val Asn Pro Asn
                 85                      90                      95

100                     105                     110
Thr Pro Glu His Lys Phe Lys Ser Ile Lys Ala Gly Glu Ser Phe Asn
Ile Leu Ala Cys Tyr Glu Gly Cys Pro Gly Ser Val Tyr Gly Val Asn
            115                     120                     125

130                     135                     140
Met Arg Ser Gln Gly Thr Ile Lys Gly Ser Phe Ile Ala Gly Thr Cys
Gly Ser Val Gly Tyr Val Leu Glu Asn Gly Ile Leu Tyr Phe Val Tyr
145                     150                     155                     160

165                     170                     175
Met His His Leu Glu Leu Gly Asn Gly Ser His Val Gly Ser Asn Phe
Glu Gly Glu Met Tyr Gly Gly Tyr Glu Asp Gln Pro Ser Met Gln Leu
            180                     185                     190

195                     200                     205
Glu Gly Thr Asn Val Met Ser Ser Asp Asn Val Val Ala Phe Leu Tyr
Ala Ala Leu Ile Asn Gly Glu Arg Trp Phe Val Thr Asn Thr Ser Met
        210                     215                     220

225                     230                     235                     240
Ser Leu Glu Ser Tyr Asn Thr Trp Ala Lys Thr Asn Ser Phe Thr Glu
Leu Ser Ser Thr Asp Ala Phe Ser Met Leu Ala Ala Lys Thr Gly Gln
                245                     250                     255

260                     265                     270
Ser Val Glu Lys Leu Leu Asp Ser Ile Val Arg Leu Asn Lys Gly Phe
Gly Gly Arg Thr Ile Leu Ser Tyr Gly Ser Leu Cys Asp Glu Phe Thr
        275                     280                     285

Pro Thr Glu Val Ile Arg Gln Met Tyr Gly Val Asn Leu Gln
        290                     295                     300
```

Analysis of the binding mode of this inhibitor shows that it is similar to that seen for an inhibitor of the distantly related human rhinovirus 3C proteinase. On the basis of the combined structural information, a group of prototype inhibitors [1,] is proposed that should block all these enzymes and thus be suitable drugs targeting a majority of viral infections of the respiratory tract, including SARS.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further advantages and features of the invention can be gathered from the following description of a preferred embodiment of the invention with reference to the attached drawings, wherein:

FIG. 1B illustrates a structure-based sequence alignment of the main proteinases of coronaviruses from all three groups including HCoV, human coronavirus 229E (group I); TGEV, porcine transmissible gastroenteritis virus (group I); MHV, mouse hepatitis virus (group II); BCoV, bovine coronavirus (group II); SCoV, SARS coronavirus (between groups II and III); and IBV, avian infectious bronchitis virus (group III);

DETAILED DESCRIPTION OF THE PREFERRED EMBODIMENT

Figure 1A:
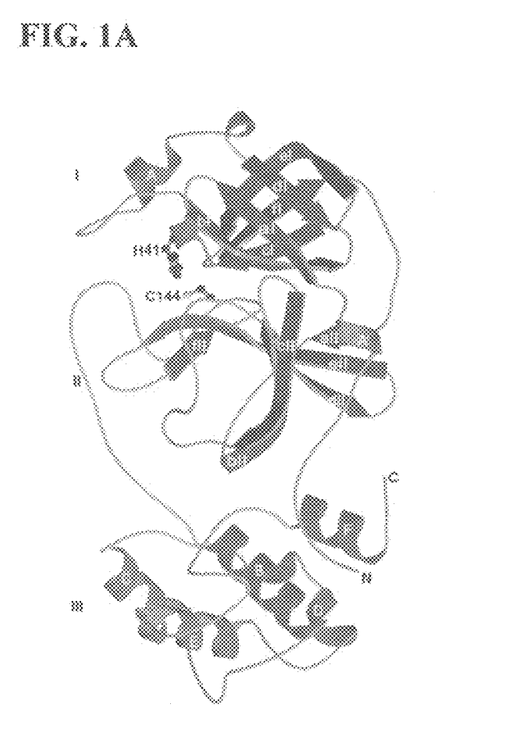
FIG. 1A illustrates a three-dimensional structure of coronavirus $M^{pro}$ (Monomer of HCoV $M^{pro}$) of the present invention, wherein domains I (top), II, and III (bottom) are indicated (helices are red and strands are green)

As shown in FIG. 1A, α-helices are labeled A to F according to occurrence along the primary structure, with the additional one-turn A' α-helix in the N-terminal segment (residues 11-14). β-strands are labeled a to f, followed by an indication of the domain to which they belong (I or II). NH$_2$- and COOH-terminus are labeled N and C, respectively. Residues of the catalytic dyad, Cys$^{144}$ and His$^{41}$, are indicated.

As shown in FIG. 1B, the autocleavage sites of the proteinases are marked by vertical arrows above the sequences. In addition to the sequences of the mature enzymes, four residues each of the viral polyprotein NH$_2$-terminal to the first and COOH-terminal to the second autocleavage site are shown. Note the conservation of the cleavage pattern, (small) Xaa-Leu-Gln↓(Ala,Ser,Gly). Thick bars above the sequences indicate α-helices (numbered A', A to F), and horizontal arrows indicate β-strands (numbered a-f, followed by the domain to which they belong). Residue numbers for HCoV M$^{pro}$ are given below the sequence (3-digit numbers are centered about the residue). Symbols in the second row below the alignment mark residues involved in dimerization of HCoV and TGEV M$^{pro}$ including open circle "o" (only main chain involved), asterisk "*" (only side chain involved), and plus "+" (both main chain and side chain involved). From the almost absolute conservation of side chains involved in dimerization, it can be concluded that SARS-CoV M$^{pro}$ also has the capacity to form dimers. In addition, side chains involved in inhibitor binding in the TGEV M$^{pro}$ complex are indicated by triangles (Δ), and catalytic-site residues Cys$^{144}$ and His$^{41}$, as well the conserved "Y$^{160}$MH$^{162}$" motif, are shaded.

Referring to FIG. 1A, the crystal structure of HCoV M$^{pro}$ shows that the molecule comprises three domains. Domains I and II (residues 8-99 and 100-183, respectively) are six-stranded antiparallel β-barrels, and together resemble the architecture of chymotrypsin and of picornavirus 3C proteinases. The substrate-binding site is located in a cleft between these two domains. A long loop (residues 184 to 199) connects domain II to the COOH-terminal domain (domain III, residues 200-300). This latter domain, a globular cluster of five helices, has been implicated in the proteolytic activity of M$^{pro}$. The HCoV M$^{pro}$ structure is very similar to that of TGEV M$^{pro}$, as produced and defined by theoretical modeling using the coordinates deposited at the Protein Data Bank under accession number PDB ID: 1P9T (Coronavirus Main Proteinase (3CLPRO) Structure: Basis for Design of Anti-Sars Drugs). The r.m.s. deviation between the two structures is ~1.5 Å for all 300° C.α positions of the molecule, but the isolated domains exhibit r.m.s. deviations of only ~0.8 Å. The construction of HCoV M$^{pro}$ used in this work lacks two amino acid residues from the COOH-terminus. HCoV M$^{pro}$ Δ (residues 301-302) has the same enzymatic properties as full-length HCoV M$^{pro}$ but yields much superior crystals. In the structure of full-length M$^{pro}$, residues 301 and 302 are disordered and not seen in the electron density. With HCoV 229E and TGEV both being group I coronaviruses, their main proteinases share 61% sequence identity.

The construction of HCoV M$^{pro}$ used in this work lacks two amino acid residues from the COOH-terminus. HCoV M$^{pro}$ Δ(301-302) has the same enzymatic properties as full-length HCoV M$^{pro}$ but yields much superior crystals. In the structure of full-length M$^{pro}$, residues 301 and 302 are disordered and not seen in the electron density.

For comparison of its enzymatic properties with those of the HCoV and TGEV M$^{pro}$s, we have expressed SARS-CoV (strain TOR2) M$^{pro}$ in E. coli (SARS-CoV M$^{pro}$ from strain TOR2, and acc. AY274119, SARS-CoV pp1a/pp1ab residues 3241 to 3544), and preliminarily characterized the proteinase. The amino-acid sequence of SARS-CoV M$^{pro}$ displays 40% and 44% sequence identity to HCoV 229E M$^{pro}$ and TGEV M$^{pro}$, respectively (see FIG. 1B for a structure-based alignment). Identity levels are 50% and 49%, respectively, between SARS-CoV M$^{pro}$ and the corresponding proteinases from the group II coronaviruses, mouse hepatitis virus (MHV), and bovine coronavirus (BCoV). Finally, M$^{pro}$ shares 39% sequence identity with avian infectious bronchitis virus (IBV) M$^{pro}$, the only group III coronavirus for which a main proteinase sequence is available. These data are in agreement with the conclusion deducible from the sequence of the whole genome that the new virus is most similar to group II coronaviruses, although some common features with IBV (group III) can also be detected. (SARS-CoV M$^{pro}$ from strain TOR2; acc: AY274119, SARS-CoV pp1a/pp1ab residues 3241 to 3544).

Figure 1C:
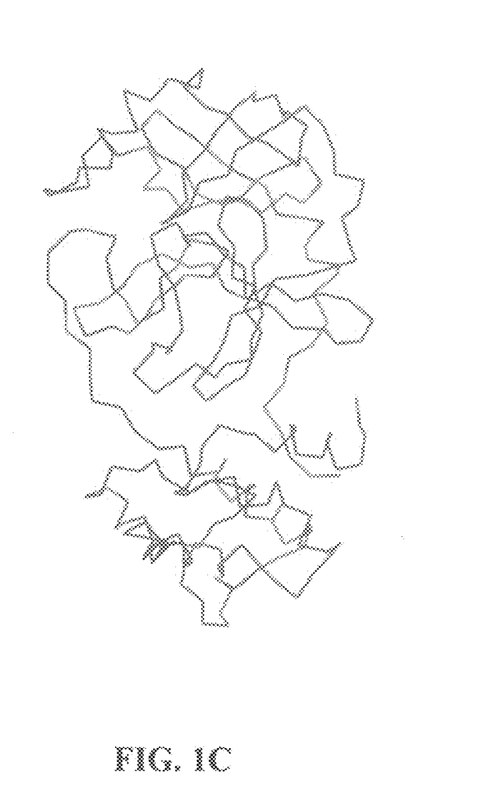
FIG. 1C illustrates a Cα plot of a monomer of $M^{pro}$ as a model-built on the basis of the crystal structures of HCoV 229E $M^{pro}$ and TGEV $M^{pro}$, wherein residues identical in HCoV $M^{pro}$ and $M^{pro}$ are indicated in red.

The level of similarity between SARS-CoV M$^{pro}$ and HCoV, as well as TGEV M$^{pro}$s, allowed us to construct a reliable three dimensional model for SARS-CoV M$^{pro}$ (See FIG. 1C). There are three 1- or 2-residue insertions in M$^{pro}$, relative to the structural templates, and as to be expected, these are all located in loops and do not present a problem in model building. Interestingly, domains I and II show a higher degree of sequence conservation (42%-48% identity) than domain III (36%-40%), between SARS-CoV M$^{pro}$ and the coronavirus group I enzymes.

Figure 2:
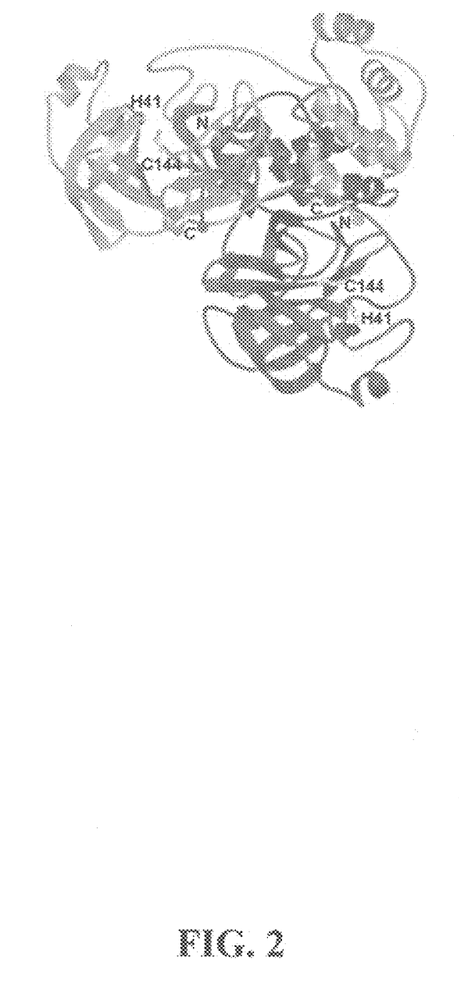
FIG. 2 illustrates a dimer of HCoV $M^{pro}$, wherein the $NH_2$-terminal residues of each chain squeeze between domains II and III of the parent monomer and domain II of the other monomer. $NH_2$- and COOH-termini are labeled by cyan and magenta spheres, and letters N and C, respectively.

HCoV 229E M$^{pro}$ forms a tight dimer (contact interface, predominantly between domain II of molecule A and the NH$_2$-terminal residues of molecule B, ~1300 Å$^2$) in the crystal, with the two molecules oriented perpendicular to one another, as indicated in FIG. 2. Our previous crystal structure of the TGEV M$^{pro}$ revealed the same type of dimer. We could show by dynamic light scattering that both HCoV and TGEV M$^{pro}$ exist as a mixture of monomers (~65%) and dimers (~35%) in diluted solutions (1-2 mg proteinase/ml). However, since the architecture of the dimers, including most details of intermolecular interaction, are the same in both TGEV M$^{pro}$ (three independent dimers per asymmetric unit) and HCoV M$^{pro}$ (one dimer per asymmetric unit), i.e., in completely different crystalline environments, we believe that dimer formation is of biological relevance in these enzymes. In the M$^{pro}$ dimer, the NH$_2$-terminal amino-acid residues are squeezed in between domains II and III of the parent monomer, and domain II of the other monomer, where they make a number of very specific interactions that appear tailor-made to bind this segment with high affinity after autocleavage. This mechanism would immediately enable the catalytic site to act on other cleavage sites in the polyprotein. However, the exact placement of the amino terminus also seems to have a structural role for the mature M$^{pro}$, since deletion of residues 1 to 5 lead to a decrease in activity to 0.3% in the standard peptide-substrate assay. Nearly all side chains of TGEV M$^{pro}$ and HCoV M$^{pro}$ involved in formation of this dimer (marked in FIG. 1B) are conserved in the SARS-CoV enzyme so that it is safe to assume a dimerization capacity for the latter, as well.

In the active site of HCoV M$^{pro}$, Cys$^{144}$ and His$^{41}$ form a catalytic dyad. In contrast to serine proteinases and other cysteine proteinases, which have a catalytic triad, there is no third catalytic residue present. HCoV M$^{pro}$ has Val$^{84}$ in the corresponding position (Cys in SARS-CoV M$^{pro}$) with its side chain pointing away from the active site. A buried water molecule is found in the place that would normally be occupied by the third member of the triad. This water is hydrogen bonded to His$^{41}$ Nδ1, Gln$^{163}$ Nε2, and Asp$^{186}$ Oδ1 (His, His, and Asp in both SARS-CoV and TGEV M$^{pro}$).

To allow structure-based design of drugs directed at coronavirus M$^{pro}$s, we sought to determine the exact binding mode of M$^{pro}$ substrates. To this end, we synthesized the substrate-analog chloromethyl ketone inhibitor Cbz-Val-Asn Ser-Thr-Leu-Gln-CMK (hereinafter 'CMK'), and soaked it into crystals of TGEV M$^{pro}$ because these were of better quality and diffracted to higher resolution than those of HCoV M$^{pro}$. The sequence of the inhibitor was derived from the P6-P1 residues of the NH$_2$-terminal autoprocessing site of TGEV M$^{pro}$ (SARS-CoV M$^{pro}$ and HCoV M$^{pro}$ have Thr-Ser-Ala-Val-Leu-Gln and Tyr-Gly-Ser-Thr-Leu-Gln, respectively, at the corresponding positions (see FIG. 1B)). X-ray crystallographic analysis at 2.37 Å resolution revealed difference densities for all residues of the inhibitor, except the benzyloxycarbonyl (Cbz) protective group, in two (B and F) out of the six TGEV M$^{pro}$ monomers in the asymmetric unit (See FIG. 3A). In these monomers, there is a covalent bond between the Sγ atom of Cys$^{144}$ and the methylene group of the chloromethyl ketone.

Figure 3A:
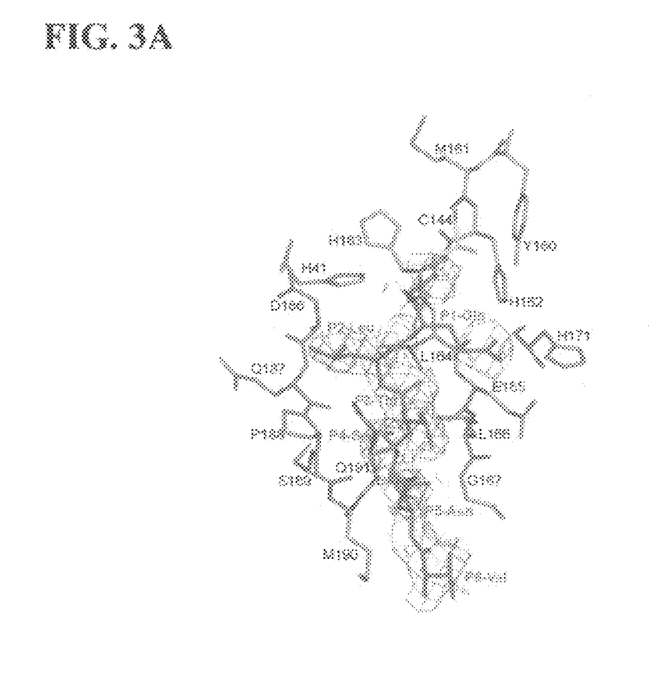
FIG. 3A illustrates a refined model of the TGEV $M^{pro}$-bound hexapeptidyl chloromethyl ketone inhibitor built into electron density (2∥Fo∣−∣Fc∥, contoured at 1σ above the mean). There was no density for the Cbz group and for the Cβ atom of the P1 Gln. The inhibitor is shown in red, protein is shown in gray, and $Cys^{144}$ is shown in yellow (Inhibitors will bind to different coronavirus $M^{pro}$s in an identical manner)

Referring still to FIG. 3A, there are no significant differences between the structures of the enzyme in the free and in the complex state. The substrate-analog inhibitor binds in the shallow substrate-binding site at the surface of the proteinase, between domains I and II. The residues Val-Asn Ser-Thr-Leu-Gln occupy, and thereby define, the subsites S6 to S1 of the proteinase. Residues P5 to P3 form an antiparallel β-sheet with segment 164-167 of the long strand eII on one side, and they also interact with segment 189-191 of the loop linking domains II and III on the other. The functional significance of this latter interaction is supported by the complete loss of proteolytic activity upon deletion of the loop region in TGEV M$^{pro}$.

Figure 3B:
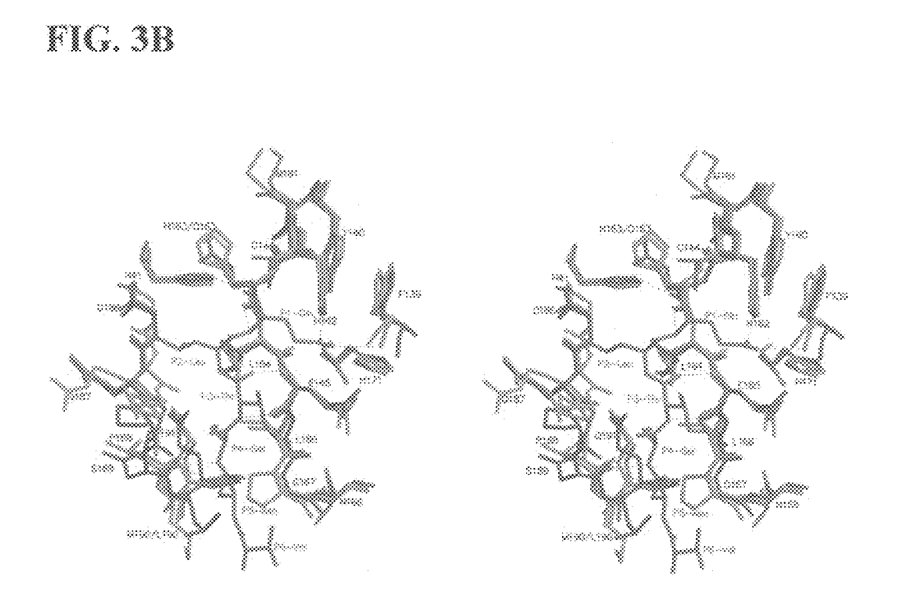
FIG. 3B illustrates a superimposition (stereo image) of the substrate-binding regions of the free enzymes of HCoV 229E $M^{pro}$ (shown in blue), SARS-CoV $M^{pro}$ (shown in magenta), and TGEV $M^{pro}$ (shown in green), in complex with the hexapeptidyl chloromethyl ketone inhibitor (shown in red), with the covalent bond between the inhibitor and $Cys^{144}$ of TGEV $M^{pro}$ shown in orange.

In coronavirus M$^{pro}$ polyprotein cleavage sites, the P1 position is invariably occupied by Gln. At the very bottom of the M$^{pro}$ S1 subsite, the imidazole of His$^{162}$ is suitably positioned to interact with the P1 glutamine side chain (See FIGS. 3A and 3B). The required neutral state of His$^{162}$ over a broad pH range appears to be maintained by two important interactions, i) stacking onto the phenyl ring of Phe$^{139}$, and ii) accepting a hydrogen bond from the hydroxyl group of the buried Tyr$^{160}$. In agreement with this structural interpretation, any replacement of His$^{162}$ completely abolishes the proteolytic activity of HCoV and feline coronavirus (FIPV) M$^{pro}$. Furthermore, FIPV M$^{pro}$ Tyr$^{160}$ mutants have their proteolytic activity reduced by a factor of >30. All of these residues are conserved in M$^{pro}$ and, in fact, in all coronavirus main proteinases. Other elements involved in the S1 pocket of the M$^{pro}$ are the main-chain atoms of Ile$^{51}$, Leu$^{164}$, Glu$^{165}$, and His$^{171}$. In M$^{pro}$, Ile$^{51}$ becomes Pro and Leu$^{164}$ is Met, although this is less relevant since these residues contribute to the subsite with their main-chain atoms only, as shown in FIG. 3B (side chains involved in specificity pockets are marked by "Δ" in FIG. 1B).

Apart from a few exceptions, coronavirus M$^{pro}$ cleavage sites have a Leu residue in the P2 position. The hydrophobic S2 subsite of the proteinase is formed by the side chains of Leu$^{164}$, Ile$^{51}$, Thr$^{47}$, His$^{41}$ and Tyr$^{53}$. The corresponding residues in SARS-CoV M$^{pro}$ are Met, Pro, Asp, His and Tyr. In addition, residues 186-188 line the S2 subsite with some of their main-chain atoms. The Leu side chain of the inhibitor is well accommodated in this pocket. As shown in FIG. 3B, it is noteworthy that M$^{pro}$ has an alanine residue (Ala$^{46}$) inserted in the loop between His$^{41}$ and Ile$^{51}$, but this is easily accommodated in the structural model and does not change the size or chemical properties of the S2 specificity site.

There is no specificity for any particular side chain at the P3 position of coronavirus M$^{pro}$ cleavage sites. This agrees with the P3 side chain of our substrate analog being oriented towards bulk solvent. At the P4 position, there has to be a small amino-acid residue, such as Ser, Thr, Val, or Pro, because of the congested cavity formed by the side chains of Leu$^{164}$, Leu$^{166}$, and Gln$^{191}$, as well as the main-chain atoms of Ser$^{189}$. These are conserved or conservatively substituted (L164M, S189T) in SARS-CoV M$^{pro}$. The P5 Asn side chain interacts with the main chain at Gly$^{167}$, Ser$^{189}$, and Gln$^{191}$ (Pro, Thr, Gln in the enzyme), thus involving the loop linking domains II and III, whereas the P6 Val residue is not in contact with the protein. Although the inhibitor used in the present study does not include a P1' residue, it is easily seen that the common small P1' residues, Ser, Ala, or Gly, can be easily accommodated in the S1' subsite of TGEV M$^{pro}$ formed by Leu$^{27}$, His$^{41}$, and Thr$^{47}$, with the latter two residues also being involved in the S2 subsite, Leu, His, and Asp in M$^{pro}$. Superimposition of the structures of the TGEV M$^{pro}$-CMK complex and the free enzyme of HCoV M$^{pro}$ shows that the two substrate binding sites are basically the same (See FIG. 3B). All residues along the P site of the cleft are identical, with the exception of the conservative M190L replacement, Ala in SARS CoV M$^{pro}$. In other coronavirus species including the SARS pathogen, M$^{pro}$ residues 167 and 187-189 show some substitutions, but since these residues contribute to substrate binding with their main-chain atoms only, the identity of the side chains is less important. Indeed, the substrate-binding site of the SARS-CoV M$^{pro}$ model matches those of its TGEV and HCoV counterparts perfectly (refer to FIG. 3B). Thus, there is no doubt that the CMK inhibitor will bind to the HCoV M$^{pro}$ and SARS-CoV M$^{pro}$ as well as all other coronavirus homologs with similar affinity and in the same way as it does to TGEV M$^{pro}$.

We developed a method to express SARS-CoV M$^{pro}$ in *E. coli*, as a fusion protein with maltose-binding protein (MBP). The free SARS-CoV M$^{pro}$ was released from this fusion protein by cleavage with factor Xa. We demonstrated that the purified, recombinant SARS-CoV M$^{pro}$ processes the peptide H$_2$N VSVNSTLQ↓SGLRKMA-COOH. Referring now to FIG. 1B, this peptide, which represents the NH$_2$-terminal autoprocessing site of TGEV M$^{pro}$ (cleavage site indicated by ↓), and contains the sequence of our CMK inhibitor, is efficiently cleaved by SARS-CoV M$^{pro}$ but not by its inactive catalytic-site mutant C145A, as shown in FIG. 4.

While peptidyl chloromethyl ketone inhibitors themselves are not useful as drugs because of their high reactivity and their sensitivity to cleavage by gastric and enteric proteinases, they are excellent substrate mimetics. With the CMK template structure at hand, comprising at least a portion of the substrate coordinates deposited at the Protein Data Bank under accession number PDB ID: 1P9U, we compared the binding mechanism to that seen in the distantly related picornavirus 3C proteinases (3C$^{pro}$). The latter enzymes have a chymotrypsin-related structure, similar to domains I and II of HCoV M$^{pro}$, although some of the secondary-structure elements are arranged differently, making structural alignment difficult (sequence identity <10%). Also, they completely lack a counterpart to domain III of coronavirus M$^{pro}$s. Nevertheless, the substrate specificity of picornavirus 3C$^{pro}$s for the P1', P1 and P4 sites is very similar to that of the coronavirus M$^{pro}$s.

Figure 4:
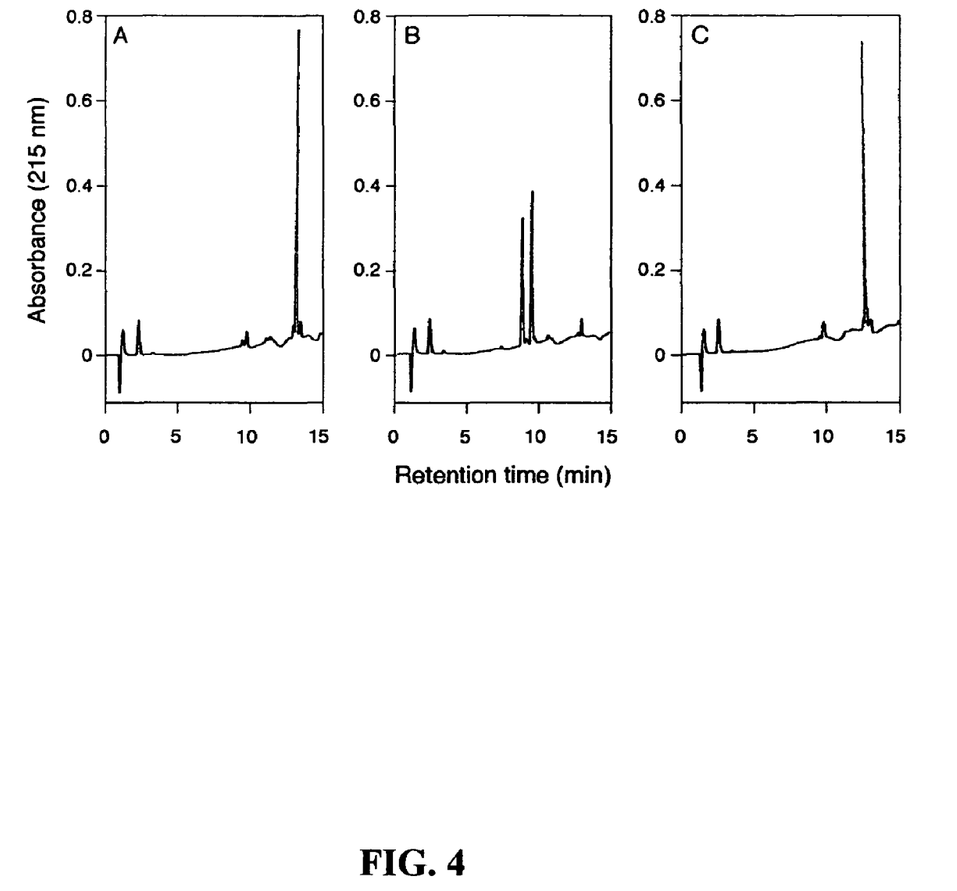
FIG. 4 illustrates a TGEV $M^{pro}$ cleavage site which is recognized and cleaved by recombinant SARS-CoV $M^{pro}$. The peptide $H_2$N-VSVNSTLQ↓SGLRKMA-COOH (vertical arrow indicates the cleavage site), representing the $NH_2$-terminal autoprocessing site of TGEV $M^{pro}$, was efficiently cleaved by $M^{pro}$, but not by an inactive catalytic-site mutant of this enzyme. HPLC elution profiles of uncleaned peptide (incubated with buffer) in the absence of proteinase are represented in graph A, peptide incubated with $M^{pro}$ are represented in graph B, and peptide incubated with $M^{pro}$-C145A are represented in graph C.
Figure 5:
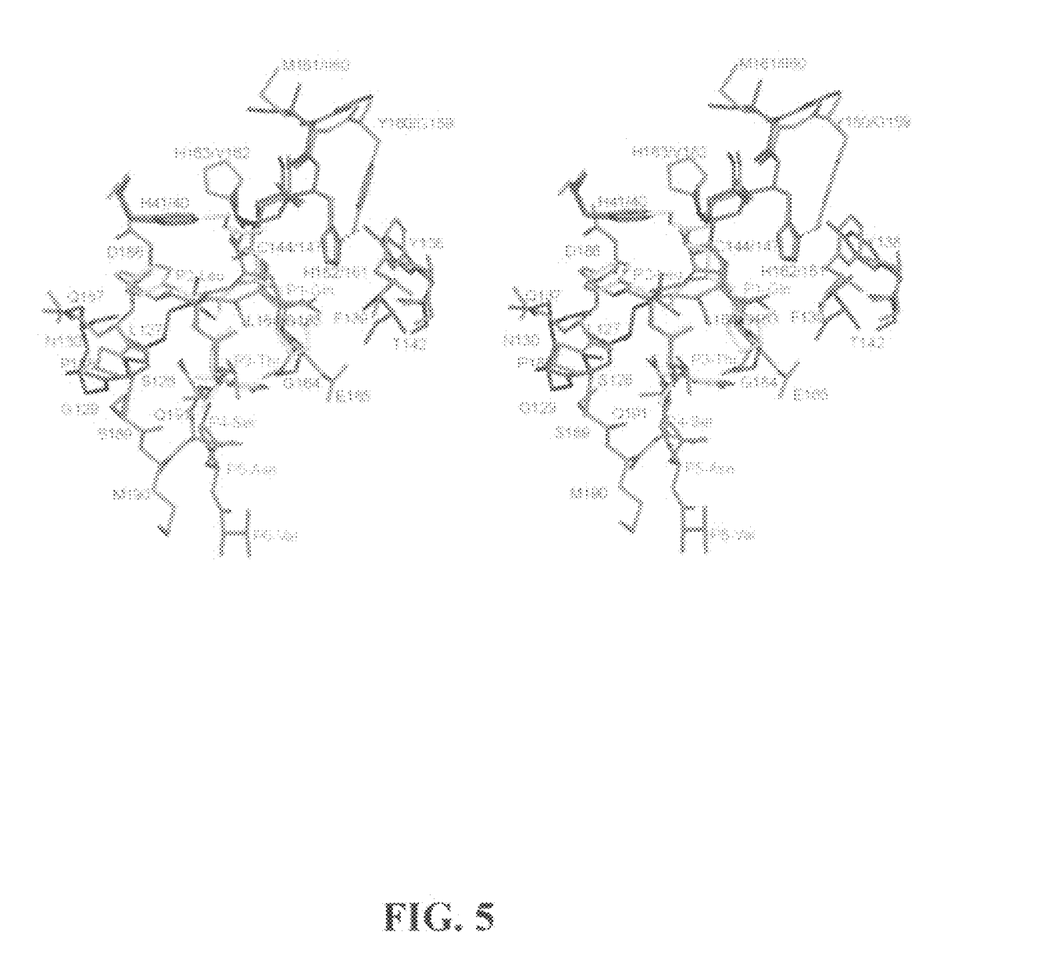
FIG. 5 illustrates derivatives of the antirhinoviral drug AG7088 that should inhibit coronavirus $M^{pro}$s. Superimposition (stereo image) of the substrate-binding regions of TGEV $M^{pro}$ (shown in green) are in complex with the hexapeptidyl chloromethyl ketone inhibitor (shown in red), and HRV2 3C$^{pro}$ (shown in marine) are in complex with the inhibitor AG7088 (shown in yellow)
Figure 6:
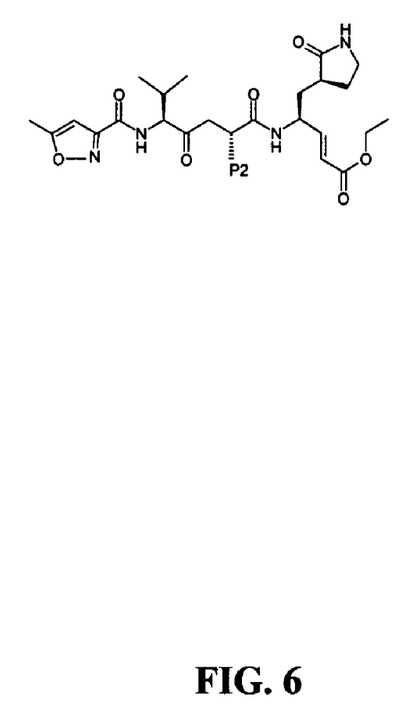
FIG. 6 illustrates derivatives of AG7088, compounds 1, proposed for inhibition of coronavirus main proteinases, including SARS coronavirus (SARS-CoV) M$^{pro}$ (P2=p-fluoro-benzyl, AG7088).

Referring still to FIG. 4, we found similar interactions between inhibitor and enzyme in case of the human rhinovirus (HRV) serotype 2 3C$^{pro}$ in complex with AG7088, an inhibitor carrying a vinylogous ethyl ester instead of a CMK group. Only parts of the two structures can be spatially superimposed (r.m.s. deviation of 2.10 Å for 134 pairs of Cα positions out of the ~180 residues in domains I and II). Both inhibitors, the hexapeptidyl chloromethyl ketone and AG7088, bind to their respective target proteinases through formation of an antiparallel β-sheet with strand ell (See FIG. 5). However, completely different segments of the polypeptide chain interact with the substrate analogs on the opposite site, with residues 188-191 of the loop connecting domains II and III in M$^{pro}$, as opposed to the short β-strand 126-128 in HRV 3C$^{pro}$. As a result, the architectures of the S2 subsites are entirely different between the two enzymes, hence, the different specificities for the P2 residues of the substrates (Leu vs. Phe). The inhibitor AG7088 has a p-fluorophenylalanine side chain (p-fluorobenzyl) in this position. Based on molecular modeling, we believe that this side chain might be too long to fit into the S2 pocket of coronavirus M$^{pro}$, but an unmodified benzyl group would probably fit, as evidenced by Phe occurring in the P2 position of the COOH-terminal autocleavage site of the SARS coronavirus enzyme (deduced from the genomic sequence referred to in FIG. 5). Apart from this difference, the superimposition of the two complexes suggests that the side chains of AG7088 binding to subsites S1 (lactone derivative of glutamine) and S4 (5-methyl-isoxazole-3-carbonyl), can be easily accommodated by the coronavirus M$^{pro}$. Thus, AG7088 could well serve as a starting point for modifications which should quickly lead to an efficient and bioavailable inhibitor for coronavirus main proteinases. Such modifications could incorporate all derivatives of the AG7088 compound with any P2 group, and more distantly related compounds such as AA1-AA2-AA3-AA4-P2-Gln-vinylogous ester (also the methyl and isopropylester, and other alkyl), with AA1, AA2, AA4 (any amino acid or absent), AA3 (small, such as Thr, Val, Ser, Ala), P2 (Leu, Phe, Met), and derivatives thereof (refer to FIG. 6).

Since AG7088 is already clinically tested for treatment of the "common cold" (targeted at rhinovirus 3C$^{pro}$) and since there are no cellular proteinases with which the inhibitors could interfere, prospects for developing broad-spectrum antiviral drugs on the basis of the structures presented here are good. Such drugs can be expected to be active against several viral proteinases exhibiting Gln↓(Ser,Ala,Gly) specificity, including the SARS coronavirus enzyme.

The structural information provided herein can be utilized to design or identify novel peptide drugs using, for example, a rational drug design (RDD) approach. Software applications typically utilized for such purposes include RIBBONS, Carson, M., 1997, *Methods in Enzymology*, 277, P. 25; O, Jones, T A., et al., 1991, *Acta Crystallogr, A*47, P. 110; DINO, *DINO: Visualizing Structural Biology*, 2001, http://www.dzno3d.org; and QUANTA, CHARMM, INSIGHT, SYBYL, MACROMODE, ICM, MOLMOL, RASMOL and GRASP, reviewed in Kraulis, J., 1991, *Appl. Crystallogr.*, 24, P. 946. Additional information regarding RDD can be found in *Rational Drug Design by Truhlar*, et al, 1999, Springer-Verlag, Incorporated, New York.

The term "peptide" as used herein encompasses native peptides, either degradation products, synthetically synthesized peptides or recombinant peptides, and peptidomimetics, typically, synthetically synthesized peptides, as well as peptoids and semipeptoids which are peptide analogs, which may have, for example, modifications rendering the peptides more stable while in a body or more capable of penetrating into cells. Such modifications include, but are not limited to, N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in *Quantitative Drug Design*, C. A. Ramsden Gd., Chapter 17.2, F. Choplin Pergamon Press, 1992. Further details in this respect are provided hereinbelow.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), and α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), or peptide derivatives (—N(R)—CH2-CO—), with R being the "normal" side chain naturally presented on the carbon atom. These modifications can occur at any of the bonds along the peptide chain and even at several (2-3) at the same time. Natural aromatic amino acids, Trp, Tyr and Phe, may be substituted for synthetic non-natural acid such as TIC, naphthylelanine (Nol), ring methylated derivatives of Phe, halogenated derivatives of Phe or o-methyl-Tyr.

In addition to the above, the peptides of the present invention may also include one or more modified amino acids or one or more non-amino acid monomers, e.g., fatty acids, complex carbohydrates, etc. The term "amino acid" or "amino acids" is understood to include the 20 naturally occurring amino acids, those amino acids often modified post translationally in vivo, including, for example, hydroxyproline, phosphor serine and phosphothreonine, and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The peptides of the present invention are preferably utilized in a linear form, although it will be appreciated that in cases where cyclization does not severely interfere with peptide characteristics, cyclic forms of the peptide can also be utilized. The peptides may be synthesized by any techniques that are known to those skilled in the art of peptide synthesis. For solid phase peptide synthesis, a summary of the many techniques may be found in J. M. Stewart and J. D. Young, *Solid Phase Peptide Synthesis*, W. H. Freeman Co., San Francisco, 1963, and J. Meienhofer, *Hormonal Proteins and Peptides*, vol. 2, P. 46, Academic Press, New York, 1973. For classical solution synthesis see G. Schroder and K. Lupke, *The Peptides*, vol. 1, Academic Press, New York, 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue, and the next amino acid (suitably protected) is then added, and so forth. After all the desired amino acids have been linked in the proper sequence, any remaining protecting groups (and any solid support) are removed sequentially or concurrently to afford the final peptide compound. By simple modification of this general procedure, it is possible to add more than one amino acid at a time to a growing chain, i.e., by coupling (under conditions which do not racemize chiral centers) a protected tripeptide with a properly protected dipeptide, to form, after deprotection, a pentapeptide, and so forth. A further description of peptide synthesis is disclosed in U.S. Pat. No. 6,472,505.

A preferred method of preparing the peptide compounds of the present invention involves solid phase peptide synthesis. Large scale peptide synthesis is described by *Andersson Biopolymers*, 55, P. 227-250, 2000. The peptides can be provided to the subject per se, or as part of a pharmaceutical composition where it is mixed with a pharmaceutically acceptable carrier.

As used herein, a "pharmaceutical composition" refers to a preparation of one or more of the active ingredients described herein with other chemical components, such as physiologically suitable carriers and excipients. The purpose of a pharmaceutical composition is to facilitate administration of a compound to an organism. Herein the term "active ingredient" refers to the preparation accountable for the biological effect. Hereinafter, the phrases "physiologically acceptable carrier" and "pharmaceutically acceptable carrier", which may be interchangeably used, refer to a carrier or a diluents that does not cause significant irritation to an organism, and does not abrogate the biological activity and properties of the administered compound. An adjuvant is included under these phrases.

Since activity of peptides is directly correlated with a molecular weight thereof, and measures are taken to conjugate the peptides of the present invention to high molecular weight carriers. Such high molecular weight carriers include, but are not limited to, polyalkylene glycol and polyethylene glycol (PEG), which are biocompatible polymers with a wide range of solubility in both organic and aqueous media, (Mutter et al, 1979).

Alternatively, microparticles, such as microcapsules or cationic lipids can serve as the pharmaceutically acceptable carriers of this aspect of the present invention. As used herein, microparticles include liposomes, virosomes, microspheres and microcapsules formed of synthetic and/or natural polymers. Methods for making microcapsules and microspheres are known to the skilled in the art and include solvent evaporation, solvent casting, spray drying and solvent extension. Examples of useful polymers which can be incorporated into various microparticles include polysaccharides, polyanhydrides, polyorthoesters, polyhydroxides and proteins and peptides. Liposomes can be generated by methods well known in the art such as those reported by Kim, et al., *Biochim. Biophys. Acta.*, 728, P. 339-348, 1983; Liu et al., *Biochim. Biophys. Acta.*, 1104, P. 95-101, 1992; Lee et al., *Biochim. Biophys. Acta*, 1103, P. 185-197, 1992; and Wang et al., *Biochem.*, 28, P. 9508-9514, 1989.

Alternatively, the peptide molecules of this aspect of the present invention can be incorporated within microparticles, or bound to the outside of the microparticles, either ionically or covalently.

As mentioned hereinabove, the pharmaceutical compositions of this aspect of the present invention may further include excipients. The term "excipient", refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols. Techniques for formulation and administration of drugs may be found in *Remington's Pharmaceutical Sciences*, Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections. Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes. The peptide or peptides can be formulated into a composition in a neutral or salt form. Pharmaceutically acceptable salts include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Pharmaceutical compositions for use in accordance with the present invention may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture and processing the mixture of granules, after adding suitable auxiliaries if desired, to obtain tablets or dragee cores. Suitable excipients are, in particular, fillers such as sugars including lactose, sucrose, mannitol, or sorbitol, cellulose preparations such as maize starch, wheat starch, rice starch, potato starch, gelatin, gum tragacanth, methyl cellulose, hydroxypropylmethyl-cellulose, sodium carbomethylcellulose, and/or physiologically acceptable polymers such as polyvinylpyrrolidone (PVP). If desired, disintegrating agents may be added such as cross-linked polyvinyl pyrrolidone, agar, or alginic acid or a salt such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin, as well as soft sealed capsules made of gelatin, and a plasticizer such as glycerol or sorbitol. The push-fit capsules may contain the active ingredients in admixture with fillers such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges, e.g., gelatin for use in a dispenser, may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances which increase the viscosity of the suspension such as sodium carboxymethyl cellulose, sorbitol or dextrin. Optionally, the suspension may also contain suitable stabilizers or agents which increase the solubility of the active ingredients to allow for the preparation of highly concentrated solutions. Alternatively, the active ingredient may be in powder form for constitution with a suitable vehicle, e.g., sterile, pyrogen free water based solution, before use.

The preparation of the present invention may also be formulated in rectal compositions such as suppositories or retention enemas using conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated. Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans. Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in humans. The dosage may vary depending upon the dosage form employed and the route of administration utilized.

The exact formulation, route of administration, and dosage can be chosen by the individual physician in view of the patient's condition. (See Fingl, et al., 1975, *The Pharmacological Basis of Therapeutics*, Ch. 1, P. 1).

Depending on the severity and responsiveness of the condition to be treated, dosing can be of a single or a plurality of administrations with course of treatment lasting from several days to several weeks, or until a cure is effected or diminution of the disease state is achieved. The amount of a composition to be administered will, of course, be dependent upon the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Pharmaceutical compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals which notice is reflective of approval by the agency of the form of the compositions or human or veterinary administration. Such notice, for example, may be of labeling approved by the U.S. Food and Drug Administration for prescription drugs or of an approved product insert.

EXAMPLES

Materials and Methods

Protein Expression and Purification:

Recombinant HCoV 229E $M^{pro}\Delta(301\text{-}302)$ (residues 1 to 300; COOH-terminal residues 301 and 302 deleted) was expressed and purified essentially as described previously for the FIPV and full-length HCoV main proteinases. Briefly, fusion proteins in which the HCoV pp1a/pp1ab amino acids 2966 to 3265 had been fused to the *E. coli* maltose-binding protein (MBP), were expressed in *E. coli* TB1 cells (New England Biolabs). The fusion protein MBP-HCoV-$M^{pro}\Delta$(301-302) was purified by amylose affinity chromatography and cleaved with factor Xa to release HCoV $M^{pro}\Delta$(301-302). Subsequently, the recombinant proteinase was purified to homogeneity using phenyl Sepharose HP (Amersham Biosciences), Uno-Q (Bio-Rad Laboratories), and Superdex 75 (Amersham Biosciences) columns and concentrated to $\geq$15 mg/ml (Centricon-YM3, Millipore). SARS-CoV $M^{pro}\Delta$(305-306), which also had its two COOH-terminal residues deleted, was produced in an analogous way. As a control, a SARS-CoV M$^{pro}$ mutant (SARS-CoV M$^{pro}$Δ(305-306)-C145A) was expressed and purified in an identical manner. In the latter, the active site nucleophile, Cys$^{145}$ (corresponding to Cys$^{3385}$ of the pp1a/pp1ab polyprotein), was replaced by Ala. TGEV M$^{pro}$ was expressed and purified as described.

Preparation of Selenomethionine-Derivatized HCoV M$^{pro}$:

To produce selenomethionine (SeMet)-substituted protein, the coding sequence of the MBP-HCoV-M$^{pro}$Δ(301-302) fusion protein was amplified by PCR and inserted into the unique NcoI site of pET-lid plasmid DNA (Novagen). The resulting plasmid, pET-HCoV-M$^{pro}$Δ(301-302), was used to transform the methionine auxotrophic 834(DE3) E. coli strain (Novagen), which was propagated in minimal medium containing 40 µg/ml seleno-L methionine. The SeMet-substituted HCoV M$^{pro}$Δ(301-302) was purified as described above and concentrated to 7.1 mg/ml (Centricon-YM3, Millipore).

Dynamic Light Scattering:

DLS experiments were performed using a DynaPro 801 device (Protein Solutions) with sample volumes of 15 µl.

Cleavage of a TGEV M$^{pro}$ Cleavage Site by Recombinant SARS-CoV M$^{pro}$:

The peptide used in this assay was H$_2$N-VSVNSTLQSGL-RKMA-COOH which represents the NH$_2$-terminal autocleavage site of TGEV M$^{pro}$, and corresponds to TGEV pp1a/pp1ab residues 2871-2885. The SARS-CoV M$^{pro}$Δ(305-306) and M$^{pro}$(305-306)-C145A proteins (each at 0.5 µM) were incubated with 0.25 mM of the peptide for 45 min at 25° C. in a buffer consisting of 20 mM Tris-HCl, pH 7.5, 200 mM NaCl, 1 mM EDTA, and 1 mM dithiothreitol. HPLC analysis of the cleavage reactions was done on a Delta Pak C$_{18}$ column as described previously.

Synthesis and Purification of the Hexapeptidyl Chloromethyl Ketone (Cbz-Val-Asn-Ser-Thr-Leu-Gln-CMK):

Peptide synthesis was performed on an Applied Biosystems 433A peptide synthesizer using standard Fmoc-solid phase peptide synthesis protocols. The reverse-phase HPLC chromatogram showed well-resolved peaks corresponding to the free NH$_2$-terminal peptide, and the desired peptide carrying the Cbz group at the NH$_2$-terminal valine. The identity of the product was confirmed by mass spectrometry. Conversion of the free COOH-terminal of the purified, NH$_2$-protected peptide to the chloromethyl ketone functionality was performed as previously reported. The product was then again purified by RP-HPLC, and its identity confirmed by mass spectrometry.

Crystallization:

Selenomethionine-HCoV M$^{pro}$Δ(301-302) crystals were grown at 10° C. in hanging drops by equilibration of 7.1 mg/ml protein in 11 mM Tris-HCl (pH 8.0), 200 mM NaCl, 0.1 mM EDTA, 1 mM DTT, 1% 1,6-hexanediol, and 10% polyethylene glycol 10,000 against 20% polyethylene glycol 10,000, 2% 1,6-hexanediol, 5 mM DTT, 12% dioxane and 100 mM HEPES, pH 8.5. Within about a week, fragile, plate-like crystals (~0.2×0.2×0.05 mm$^3$) were obtained. Crystals displayed space group P2$_1$ with unit cell dimensions a=53.3 Å, b=76.1 Å, c=73.4 Å, β=103.7°, and two proteinase monomers per asymmetric unit. TGEV M$^{pro}$ crystals were grown as described previously, and soaked for 16 h in a fivefold molar access of Cbz-Val-Asn-Ser-Thr-Leu-Gln-CMK, dissolved in a 1:1 mixture of dimethyl sulfoxide and acetonitrile. These crystals displayed space group P2$_1$ with unit cell dimensions a=72.4 Å, b=158.5 Å, c=88.2 Å, β=94.4°, and six proteinase molecules per asymmetric unit.

Collection of Diffraction Data:

Using a Mar345 detector (X-ray Research), diffraction data from crystals of SeMet-HCoV M$^{pro}$Δ(301-302) were collected at 100 K using synchrotron radiation at the XRD beamline of ELETTRA (Sincrotrone Trieste, Italy) at four different wavelengths around the selenium absorption edge (see Table 1). Due to the high concentration of polyethylene glycol in the mother liquor, these crystals did not require any cryoprotectant. Crystals of TGEV M$^{pro}$ that had been soaked with hexapeptidyl chloromethyl ketone inhibitor were rinsed with mustard oil before cryo-cooling in liquid nitrogen. A full diffraction data set was collected at 100 K, using the Joint IMB Jena/University of Hamburg/EMBL synchrotron beamline X13 at DESY (Hamburg, Germany) at a wavelength of 0.802 Å and equipped with a MarCCD detector (X-ray Research). For both proteins, diffraction data were processed using the DENZO and SCALEPACK programs. Diffraction data statistics are given in TABLE 1.

Structure Solution:

The anomalous signal from selenium in crystals of HCoV M$^{pro}$Δ(301-302) was weak and did not provide sufficient phase information for solving the structure. Therefore, data collected at all four wavelengths were merged and used for structure elucidation by molecular replacement using AMoRe, with a monomer of TGEV M$^{pro}$ as the search model (See TABLE 2). The structure of TGEV M$^{pro}$ in complex with the hexapeptidyl chloromethyl ketone inhibitor was determined by different Fourier methods. The maps showed density for all residues (except the benzyloxycarbonyl (Cbz) protective group) of the inhibitor in the substrate-binding sites of monomers B and F. Density was weak at the Cβ atom of the P1 Gln residue, but the orientation of this side chain was still well defined due to the strong density for the carboxamide group. Density was also relatively weak for the side chains of the P5 and P6 residues of the inhibitor, indicating high mobility (particularly in the complex with monomer F). There was only little difference density near the S2 subsite in the substrate-binding clefts of the remaining four monomers, A, C, D, and E, indicating that these sites were occupied by 2-methyl-2,4-pentanediol (MPD) molecules from the crystallization medium, as in the free TGEV M$^{pro}$.

Model Building and Refinement:

Both the HCoV M$^{pro}$ and TGEV M$^{pro}$ CMK complex models were refined using CNS. A random set of reflections containing 4% of the total data was excluded from the refinement for calculation of R$_{free}$. Model building was carried out using the program 'O'. σ$_A$-weighted maps were used to avoid model bias. All residues of the HCoV M$^{pro}$Δ(301-302) dimer were in unambiguous electron density. The final model comprises 600 amino-acid residues, 2 dioxane molecules and 221 water molecules. For the TGEV M$^{pro}$ complex structure, all amino-acid residues in all six copies of the protein had well-defined electron density, with the exception of residues 301 and 302. The final model comprises 1799 amino-acid residues, 2 hexapeptidyl chloromethyl ketones, 4 MPD molecules, 27 sulfate ions, and 925 water molecules. Refinement statistics are summarized in TABLE 3.

Homology Model Building:

Insight II (Molecular Simulations) was used to construct the three-dimensional model for SARS-CoV M$^{pro}$ on the basis of the sequence alignment with HCoV M$^{pro}$ and TGEV M$^{pro}$, and the crystal structures of these two enzymes. The model was energy minimized in Insight II and inspected for steric consistency.

Analysis of the Structural Models:

Overall geometric quality of the models was assessed using PROCHECK. For HCoV M$^{pro}$ and TGEV M$^{pro}$, respectively, 85.1% and 89.0% of the amino-acid residues were found in the most favored regions of the Ramachandran plot, and 15.5% and 10.5% were in additionally allowed regions. The corresponding numbers for the homology model of SARS-CoV M$^{pro}$ were 87.1% and 11.3%. The agreement between structure-factor data and the atomic model was analyzed using SFCHECK. Solvent accessibilities were calculated using the algorithm of Lee and Richards as implemented in the program NACCESS (probe radius 1.4 Å). Molecular diagrams were drawn using the programs MOLSCRIPT, PyMol, and RASTER 3D.

TABLE 1

Crystal Parameters and Statistics of Diffraction Data

| Diffraction data statistics | HCoV M$^{pro}$ | TGEV M$^{pro}$-CMK complex |
|---|---|---|
| Crystal Information | | |
| Space group | P2$_1$ | P2$_1$ |
| Unit cell parameters (Å, °) | a = 53.3, b = 76.1, c = 73.4, β = 103.7 | a = 72.4, b = 158.5, c = 88.2, β = 94.4 |
| Estimated solvent content$^a$ (%) | 44 | 51 |
| Diffraction data statistics | | |
| X-ray source | Synchrotron radiation$^b$ | Synchrotron radiation$^c$ |
| Detector | Mar 345 | MarCCD detector |
| No. of frames | 600 | 720 |
| Crystal oscillation (°) | 1.0 | 0.5 |
| Wavelength (Å) | 0.980 (average) | 0.802 |
| Temperature (K) | 100 | 100 |
| Resolution (Å)$^d$ | 25-2.60 (2.69-2.60) | 50-2.37 Å (2.41-2.37) |
| Completeness (%) | 98.9 | 99.8 |
| R$_{merge}$ (%)$^{d,e}$ | 14.2 (41.2)$^d$ | 8.0 (28.0)$^d$ |
| R$_{rim}$ (%)$^{d,f}$ | 14.2 (43.9)$^d$ | 2.2 (8.5)$^d$ |
| R$_{pim}$ (%)$^{d,g}$ | 3.0 (13.0)$^d$ | 0.058 (22.0)$^d$ |
| Redundancy | 12.3 | 7.1 |
| I/σ(I) | 9.1 | 9.9 |
| Mosaicity (°) | 1.80 | 0.49 |
| No. of reflections measured | 216,984 | 569,126 |
| Unique reflections | 17,533 | 79,667 |

$^a$Solvent content estimated according to B. W. Matthews, J. Mol. Biol., 33, P. 491, 1968.
$^b$X-ray diffraction beamline at ELETTRA, Trieste, equipped with a Mar345 detector.
$^c$Joint IMB Jena/University of Hamburg/EMBL synchrotron beamline X13 at Deutsches Elektronen-Synchrotron (DESY), Hamburg, equipped with a MarCCD detector.
$^d$Highest resolution bin shown in parentheses.
$^e$R$_{merge}$ = 100 × Σ$_i$Σ$_{hkl}$|I$_i$ − <I>|/Σ$_i$Σ$_{hkl}$I$_i$, where I$_i$ is the observed intensity and <I> is the average intensity from multiple measurements.
$^f$R$_{rim}$ = 100 × Σ$_i$ (N/N − 1)$^{1/2}$Σ$_{hkl}$|I$_i$ − <I>|/Σ$_i$Σ$_{hkl}$I$_i$ where N is the number of times a given reflection has been measured. This quality indicator corresponds to an R$_{sym}$ that is independent of the redundancy of the measurements, M. S. Weiss, R. Hilgenfeld, J. Appl. Crystallogr., 30, P. 203, 1997.
$^g$R$_{pim}$ = 100 × Σ$_i$ (1/N − 1)$^{1/2}$Σ$_{hkl}$|I$_i$ − <I>|/Σ$_i$Σ$_{hkl}$I$_i$. This factor provides information about the average precision of the data, M. S. Weiss, R. Hilgenfeld, J. Appl. Crystallogr., 30, P. 203, 1997.

TABLE 2

Structure solution by molecular replacement: HCoV M$^{pro}$

| Resolution range | 10.0-4.0 Å |
|---|---|
| Rotation and translation function (1$^{st}$ monomer) | |
| Best solution | α = 21.64°, β = 59.58°, γ = 256.95° |
| | tx = 0.483, ty = 0.000, tz = 0.250 Å |
| Correlation coefficient | 0.217 |
| R-factor | 51.9% |
| Rotation and translation function (2$^{nd}$ monomer) | |
| Best solution | α = 319.92°, β = 79.38°, γ = 5.39° |
| | tx = 0.054, ty = 0.481, tz = 0.785 Å |
| Correlation coefficient | 0.213 |
| R-factor | 52.1% |

TABLE 2-continued

Structure solution by molecular replacement: HCoV M$^{pro}$

Refinement of combined solution

| Monomer 1 | α = 21.80°, β = 60.40°, γ = 257.02° |
|---|---|
| | tx = 0.478, ty = −0.002, tz = 0.250 Å |
| Monomer 2 | α = 320.45°, β = 79.89°, γ = 5.89° |
| | tx = 0.057, ty = 0.482, tz = 0.784 Å |
| Correlation coefficient | 0.30 |
| R-factor | 48.8% |

TABLE 3

Phasing and refinement statistics, and model quality

| Phasing | HCoV M$^{pro}$ | TGEV M$^{pro}$-CMk complex |
|---|---|---|
| Refinement | | |
| Resolution range (Å) | 25-2.6 | 50-2.37 |
| R factor$^a$ | 0.219 | 19.1 |
| R$_{free}$ | 0.283 | 23.5 |
| No. of non-hydrogen atoms (average B value (Å$^2$)) | | |
| Protein | 4594 (28.12) | 13,819 (43.0) |
| Water | 221 (24.9) | 925 (51.3) |
| MPD | — | 32 (78.6) |
| Sulfate | — | 135 (59.8) |
| Dioxane | 12 (58.39) | — |
| Substrate-analog inhibitor | — | 92 (71.0) |
| Bonds (Å) | 0.012 | 0.006 |
| Angles (°) | 1.5 | 1.3 |

$^a$R-factor = Σ (|F$_o$| − k|F$_c$|)/Σ |F$_o$|

REFERENCES

S. H. Myint, in *The Coronavirdae*, S. G. Siddell, Ed. (Plenum Press, New York, 1995), pp. 389.

C. Drosten et al., *Identification of a Novel Coronavirus in Patients with Severe Acute Respiratory Syndrome* (http://content.nejm.org/cgi/content/abstract/NEJMoa030747v2) *N. Engl. J. Med.*, in the press (2003).

T. G. Ksiazek et al., *A Novel Coronavirus Associated with Severe Acute Respiratory Syndrome* (http://content.nejm.org/cgi/content/abstract/NEJMoa030781v2) *N. Engl. J. Med.*, in the press (2003).

N. Lee et al., *A Major Outbreak of Severe Acute Respiratory Syndrome in Hong Kong* (http://content.nejm.org/cgi/content/abstract/NEJMoa030685v1) *N. Engl. J. Med.*, in the press (2003).

J. Herold, T. Raabe, B. Schelle-Prinz, S. G. Siddell, *Virology* 195, 680 (1993).

V. Thiel, J. Herold, B. Schelle, S. G. Siddell, *J. Gen. Virol.* 75, 6676 (2001).

J. Ziebuhr, J. Herold, S. G. Siddell, *J. Virol.* 69, 4331 (1995).

J. Ziebuhr, E. J. Snijder, A. E. Gorbalenya, *J. Virol.* 81, 853 (2000).

A. Hegyi, J. Ziebuhr, *J. Gen. Virol.* 83, 595 (2002).

K. Anand et al., *EMBO J.* 21, 3213 (2002).

M. Marra et al., http://www.bcgsc.ca/bioinfo/SARS/

D. A. Matthews et al., *Proc. Natl. Acad. Sci. USA* 96, 11000 (1999).

J. Ziebuhr, G. Heusipp, S. G. Siddell, *J. Virol.* 71, 3992 (1997).

S. G. Siddell, in *The Coronaviridae*, S. G. Siddell, Ed. (Plenum Press, New York, 1995), p. 1

A. Hegyi, A. Friebe, A. E. Gorbalenya, J. Ziebuhr, *J. Gen. Virol.* 83, 581 (2002).
H. G. Kräusslich, E. Wimmer, *Annu. Rev. Biochem.* 57, 701 (1988).
M. D. Ryan, M. Flint, *J. Gen. Virol.* 78, 699 (1997).
G. B. Fields, R. L. Noble, *Int. J. Pept. Prot. Res.* 35, 161 (1990).
A. Krantz, L. J. Copp, P. J. Coles, R. A. Smith, S. B. Heard, *Biochemistry* 30, 4678 (1991).
Z. Otwinowski, W. Minor *Methods Enzymol.* 276, 307 (1997).
J. Navaza, *Acta Crystallogr.* A50, 157 (1994).
A. T. Brünger et al., *Acta Crystallogr.* D54, 905 (1998).
A. T. Brünger, *Nature* 355, 472 (1992).
T. A Jones, S. Cowan, J-Y. Zou, M. Kjeldgaard, *Acta Crystallogr.* A47, 110 (1991).
R. J. Read, *Acta Crystallogr.* A42, 140 (1986).
R. A. Laskowski, M. W. MacArthur, D. S. Moss, J. M. Thornton, *J. Appl. Crystallogr.* 26, 283 (1993).
A. A. Vaguine, J. Richelle, S. J. Wodak, *Acta Crystallogr.* D55, 191 (1999).
B. Lee, F. M. Richards, *J. Mol. Biol.* 55, 379 (1971).
P. J. Kraulis, *J. Appl. Crystallogr.* 24, 946 (1991).
W. L. DeLano, *The PyMOL Molecular Graphics System.* DeLano Scientific, San Carlos, Calif., USA. http://www.pymol.org/ (2002).
E. A. Merritt, D. J. Bacon, *Meth. Enzymol.* 277, 505 (1997).
B. W. Matthews, *J. Mol. Biol.* 33, 491 (1968).
M. S. Weiss, R. Hilgenfeld, *J. Appl. Crystallogr.* 30, 203 (1997).

Having thus described the invention, what is claimed and desired to be secured by Letters Patent is:

1. A substance with the structural formula:

wherein a residue P2 is a side chain fitting in an S2 pocket of coronavirus main proteinases, and wherein P2 is an unmodified benzyl group.

2. The substance according to claim 1, wherein said substance is prepared as a pharmaceutical composition for application to an animal or human being having a coronavirus.

3. The substance according to claim 1, wherein the coronavirus is SARS coronavirus.

4. A method for treating a coronavirus comprising administering a substance with the structural formula:

wherein a residue P2 is a side chain fitting in an S2 pocket of coronavirus main proteinases, and wherein P2 is an unmodified benzyl group.

5. The method of treating a coronavirus according to claim 4, wherein the coronavirus is SARS coronavirus.

* * * * *

SEQUENCE LISTING

```
<160> NUMBER OF SEQ ID NOS: 1

<210> SEQ ID NO 1
<211> LENGTH: 302
<212> TYPE: PRT
<213> ORGANISM: Transmissible Gastroenteritis Virus (TGEV)
<300> PUBLICATION INFORMATION:
<308> DATABASE ACCESSION NUMBER: 1P9U
<309> DATABASE ENTRY DATE: 2003-05-12
<313> RELEVANT RESIDUES IN SEQ ID NO: (1)..(302)
<300> PUBLICATION INFORMATION:
<308> DATABASE ACCESSION NUMBER: 1P9T
<309> DATABASE ENTRY DATE: 2003-05-12
<313> RELEVANT RESIDUES IN SEQ ID NO: (1)..(302)
<300> PUBLICATION INFORMATION:
<308> DATABASE ACCESSION NUMBER: 1P9S
<309> DATABASE ENTRY DATE: 2003-05-12
<313> RELEVANT RESIDUES IN SEQ ID NO: (1)..(302)

<400> SEQUENCE: 1

Ser Gly Leu Arg Lys Met Ala Gln Pro Ser Gly Leu Val Glu Pro Cys
1               5                   10                  15

Ile Val Arg Val Ser Tyr Gly Asn Asn Val Leu Asn Gly Leu Trp Leu
            20                  25                  30

Gly Asp Glu Val Ile Cys Pro Arg His Val Ile Ala Ser Asp Thr Thr
        35                  40                  45

Arg Val Ile Asn Tyr Glu Asn Glu Met Ser Ser Val Arg Leu His Asn
    50                  55                  60

Phe Ser Val Ser Lys Asn Asn Val Phe Leu Gly Val Val Ser Ala Arg
65                  70                  75                  80

Tyr Lys Gly Val Asn Leu Val Leu Lys Val Asn Gln Val Asn Pro Asn
                85                  90                  95

Thr Pro Glu His Lys Phe Lys Ser Ile Lys Ala Gly Glu Ser Phe Asn
            100                 105                 110

Ile Leu Ala Cys Tyr Glu Gly Cys Pro Gly Ser Val Tyr Gly Val Asn
        115                 120                 125

Met Arg Ser Gln Gly Thr Ile Lys Gly Ser Phe Ile Ala Gly Thr Cys
    130                 135                 140

Gly Ser Val Gly Tyr Val Leu Glu Asn Gly Ile Leu Tyr Phe Val Tyr
145                 150                 155                 160

Met His His Leu Glu Leu Gly Asn Gly Ser His Val Gly Ser Asn Phe
                165                 170                 175

Glu Gly Glu Met Tyr Gly Gly Tyr Glu Asp Gln Pro Ser Met Gln Leu
            180                 185                 190
```

| | | | | | | | | | | | | | |
|---|---|---|---|---|---|---|---|---|---|---|---|---|---|
-continued
| Glu | Gly | Thr | Asn | Val | Met | Ser | Ser | Asp | Asn | Val | Val | Ala | Phe | Leu | Tyr |
| | | 195 | | | | | 200 | | | | | 205 | | | |
| Ala | Ala | Leu | Ile | Asn | Gly | Glu | Arg | Trp | Phe | Val | Thr | Asn | Thr | Ser | Met |
| | 210 | | | | | 215 | | | | | 220 | | | | |
| Ser | Leu | Glu | Ser | Tyr | Asn | Thr | Trp | Ala | Lys | Thr | Asn | Ser | Phe | Thr | Glu |
| 225 | | | | | 230 | | | | | 235 | | | | | 240 |
| Leu | Ser | Ser | Thr | Asp | Ala | Phe | Ser | Met | Leu | Ala | Ala | Lys | Thr | Gly | Gln |
| | | | 245 | | | | | 250 | | | | | 255 | | |
| Ser | Val | Glu | Lys | Leu | Leu | Asp | Ser | Ile | Val | Arg | Leu | Asn | Lys | Gly | Phe |
| | | | 260 | | | | | 265 | | | | | 270 | | |
| Gly | Gly | Arg | Thr | Ile | Leu | Ser | Tyr | Gly | Ser | Leu | Cys | Asp | Glu | Phe | Thr |
| | | 275 | | | | | 280 | | | | | 285 | | | |
| Pro | Thr | Glu | Val | Ile | Arg | Gln | Met | Tyr | Gly | Val | Asn | Leu | Gln |
| | 290 | | | | | 295 | | | | | 300 | | |